(12) United States Patent
Polikarpus

(10) Patent No.: US 6,365,036 B1
(45) Date of Patent: Apr. 2, 2002

(54) ELECTRODE INK FORMULATION FOR OXYGEN SENSOR

(75) Inventor: Kaius Kiiren Polikarpus, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/519,244

(22) Filed: Mar. 6, 2000

(51) Int. Cl.$^7$ .............................................. G01N 27/407
(52) U.S. Cl. ..................... 205/784.5; 204/424
(58) Field of Search ................. 204/421–429; 205/784.5; 419/9, 36; 427/125, 126.3, 126.4

(56) References Cited

U.S. PATENT DOCUMENTS

| | | | |
|---|---|---|---|
| 3,843,400 A | * 10/1974 | Radford et al. | 204/421 |
| 3,914,169 A | * 10/1975 | Horowitz | 204/427 |
| 4,221,650 A | * 9/1980 | Friese et al. | 204/429 |
| 4,582,657 A | * 4/1986 | Shibata et al. | 204/429 |
| 4,863,583 A | * 9/1989 | Kurachi et al. | 204/424 |
| 5,887,240 A | 3/1999 | Fournier et al. | |
| 6,007,688 A | * 12/1999 | Kojima et al. | 204/426 |

* cited by examiner

Primary Examiner—Robert J. Warden, Sr.
Assistant Examiner—Kaj K. Olsen
(74) Attorney, Agent, or Firm—Vincent A. Cichosz

(57) ABSTRACT

The sensor of the present invention comprises a solid electolyte with an electrode disposed on both sides thereof and an electrical lead connected to each electrode. The solid electrolyte is yttria doped zirconia. The first electrode, the sensing electrode, is exposed to the sensing gas such as an exhaust gas. The second electrode, the reference electrode, is exposed to a reference gas, wherein at least one of the sensing electrode and the reference electrode comprises a noble metal, platinum, metal oxide and alumina or in mixtures thereof.

4 Claims, 3 Drawing Sheets

ELECTRODE INK FORMULATION FOR OXYGEN SENSOR

TECHNICAL FIELD

The present invention relates generally to oxygen sensors capable of detecting oxygen. Particularly, the present invention relates to an electrode composition for an oxygen sensor.

BACKGROUND OF THE INVENTION

Exhaust sensors are used in the automotive industry to sense the composition of exhaust gases such as oxygen, hydrocarbons, and oxides of nitrogen, with oxygen sensors measuring the amounts of oxygen present in exhaust gases relative to a reference gas, such as air. A switch type oxygen sensor, generally, comprises an ionically conductive solid electrolyte material, a sensing electrode which is exposed to the exhaust gas, and a reference electrode which is exposed to the reference gas. It operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right)\ln\left(\frac{P_{O_2}^{ref}}{P_{O_2}}\right)$$

where:

E=electromotive force
R=universal gas constant
F=Faraday constant
T=absolute temperature of the gas
$P_{O2}^{ref}$ =oxygen partial pressure of the reference gas
$P_{O2}$=oxygen partial pressure of the exhaust gas The large oxygen partial pressure difference between rich and lean exhaust gas conditions creates a step-like difference in cell output at the stoichiometric point; the switch-like behavior of the sensor enables engine combustion control about stoichiometry. Stoichiometric exhaust gas, which contains unburned hydrocarbons, carbon monoxide, and oxides of nitrogen, can be converted very efficiently to water, carbon dioxide, and nitrogen by automotive three-way catalysts in automotive catalytic converters. In addition to their value for emissions control, the sensors also provide improved fuel economy and drivability.

Further control of engine combustion can be obtained using amperometric mode exhaust sensors, where oxygen is electrochemically pumped through an electrochemical cell using an applied voltage. A gas diffusion-limiting barrier creates a current limited output, the level of which is proportional to the oxygen content of the exhaust gas. These sensors typically consist of two or more electrochemical cells; one of these cells operates in potentiometric mode and serves as a reference cell, while another operates in amperometric mode and serves as an oxygen-pumping cell. This type of sensor, known as a wide range, lambda, or linear air/fuel ratio sensor, provides information beyond whether the exhaust gas is qualitatively rich or lean; it can quantitatively measure the air/fuel ratio of the exhaust gas.

The solid electrolyte commonly used in exhaust sensors is yttria-stabilized zirconia. This material is an excellent oxygen ion conductor under various exhaust conditions. The electrodes are typically platinum-based and are porous in structure to enable oxygen ion exchange at electrode/electrolyte/gas interfaces. These platinum electrodes may be co-fired or applied to a fired (densified) electrolyte element in a secondary process, such as sputtering, plating, dip coating, etc. Co-fired electrodes are often used in planar type sensor elements, in which the electrodes may reside between laminated layers, where many secondary processes are not accessible. In this case, a thick film paste is may be screen printed onto unfired (green) ceramic tape and dried. The screen-printed tapes are then stacked, laminated, cut, and fired to make sensor elements.

The materials and processes used to fabricate sensor elements often provide a source for contaminant impurities that degrade the performance of the electrochemical cell. These impurities, especially silicon-based impurities, tend to migrate by diffusion, for example in the firing process, creating a barrier to oxygen ion conduction at the electrode/electrolyte interface. There exists a need in the art for an electrode formulation that is more tolerant of material and process impurities, which will help provide a cell with low, stable electrode/electrolyte interfacial impedance.

SUMMARY OF THE INVENTION

The deficiencies of the above-discussed prior art are overcome or alleviated by the oxygen sensor, electrode, and methods of the present invention. The sensor comprises: a sensing electrode having a first electrical lead and positioned to sense a sensing gas; a reference electrode having a second electrical lead; and an electrolyte disposed between and in intimate contact with said sensing electrode and said reference electrode; wherein at least one of said sensing electrode and said reference comprises about 80 wt % to about 99.85 wt % noble metal, about 0.1 wt % to about 14 wt % non-alumina metal oxide, and about 0.05 wt % to about 6 wt % alumina, based upon the total weight of the electrode.

The electrode comprises: about 80 wt % to about 99.85 wt % noble metal, about 0.1 wt % to about 14 wt % non-alumina metal oxide, and about 0.05 wt % to about 6 wt % alumina, based upon the total weight of the electrode; wherein the electrode has a resistivity below about 500 milliohms/square at about 25° C.

The method of making the electrode comprises: forming an ink comprising about 75 wt % to about 95 wt % platinum; about 0.1 wt % to about 11 wt % non-alumina metal oxide; greater than about 0.1 wt % alumina and up to about 15 wt % fugative material, based upon the total weight of the ink; applying said ink to at least a portion of one side of a substrate; and sintering said substrate to form a first electrode on said substrate; wherein the electrode has a resistivity below about 500 milliohms/square at about 25° C.

One of the methods of making the sensor comprises: forming a first ink comprising about 75 wt % to about 95 wt % noble metal; about 0.1 wt % to about 11 wt % non-alumina metal oxide; greater than about 0.1 wt % alumina and up to about 15 wt % fugative material, based upon the total weight of said first ink; applying said first ink to at least a portion of a first side of a first substrate; applying a second ink to at least a portion of a second side of a second substrate; contacting electrical leads to said first ink and said second ink; disposing an electrolyte between and in physical contact with said first side and said second side to form an assembly; forming a protective layer over said first substrate; and sintering said assembly to form the sensor having an electrode having a resistivity below about 500 milliohms/square at about 25° C.

Another method of making the sensor comprises: forming a first ink comprising about 75 wt % to about 95 wt % platinum; about 0.1 wt % to about 11 wt % non-alumina metal oxide; greater than about 0.1 wt % alumina and up to about 15 wt % fugative material, based upon the total weight of said first ink; applying said first ink to at least a portion of a first side of an electrolyte; applying a second ink to at least a portion of a second side of said electrolyte to form an assembly; connecting electrical leads to said first ink and to said second ink; forming a protective layer over said first side; and sintering said assembly to form the sensor having an electrode having a resistivity below about 500 milliohms/square at about 25° C.

Finally, one method of sensing exhaust gas comprises: using a sensor comprising a sensing electrode having a first electrical lead, a reference electrode having a second electrical lead, and an electrolyte disposed between and in intimate contact with said sensing electrode and said reference electrode; wherein at least one of said sensing electrode and said reference electrode comprises about 80 wt % to about 99.85 wt % noble metal, about 0.1 wt % to about 14 wt % non-alumina metal oxide, and about 0.05 wt % to about 6 wt % alumina, based upon the total weight of the electrode; disposing said sensor in an exhaust stream; and contacting said sensing electrode with exhaust gas.

The above-discussed and other features and advantages of the present invention will be appreciated and understood by those skilled in the art from the following detailed description and drawings.

BRIEF DESCRIPTION OF THE DRAWINGS

The present invention will now be described by way of examples with reference to the following figures, that are meant to be exemplary, not limiting, and in which.

DESCRIPTION OF THE INVENTION

Figure 1:
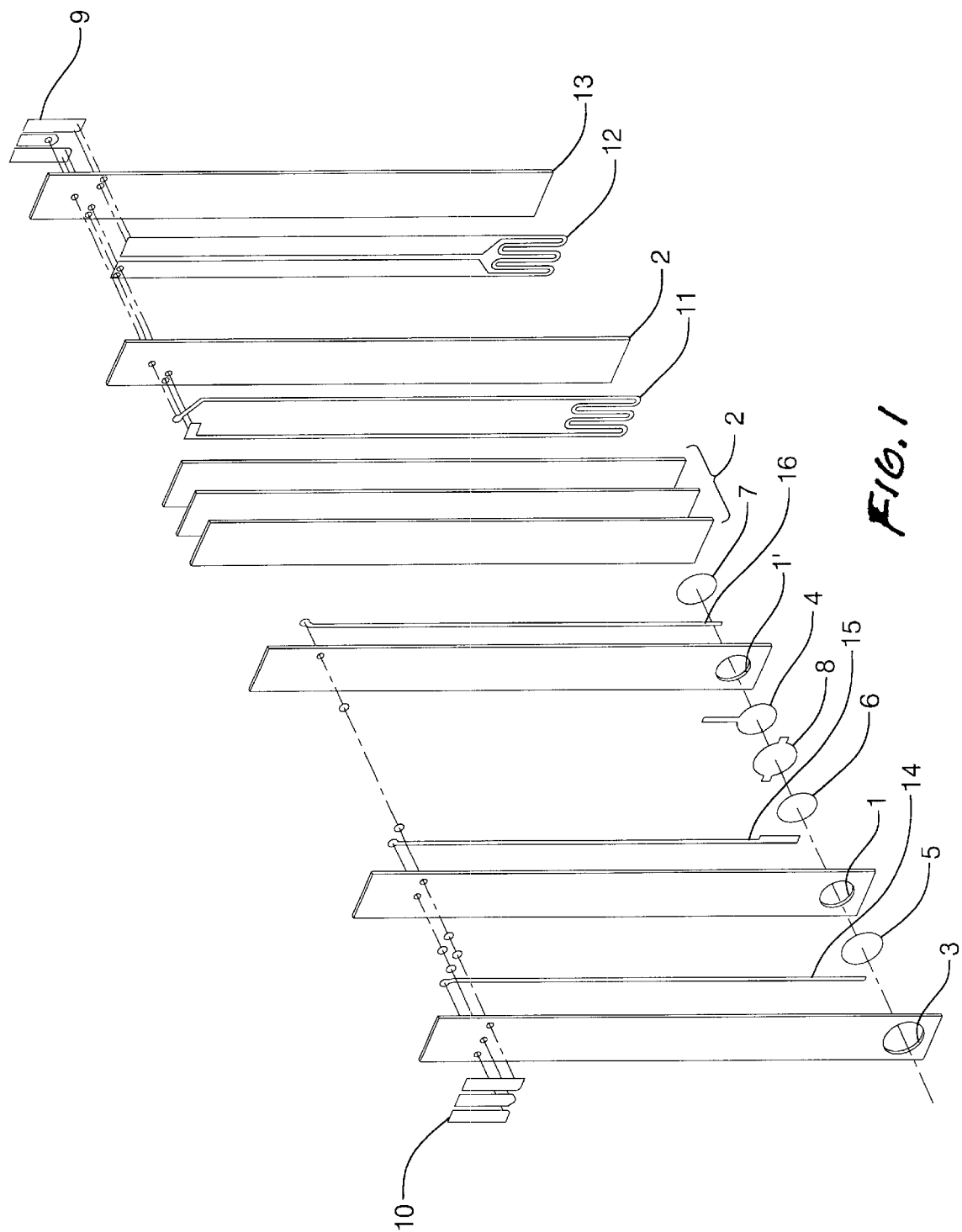
FIG. 1 is an example of an oxygen sensor.
Figure 2:
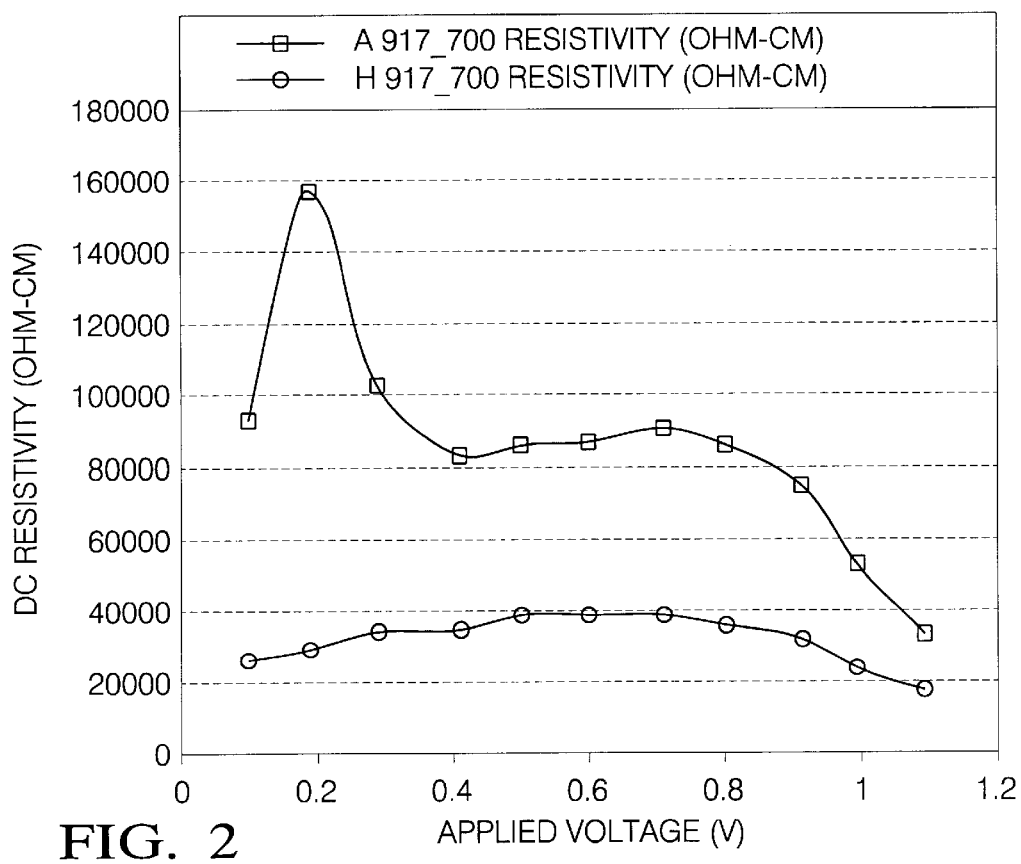
FIG. 2 is a graphical representation of the resistivity versus applied voltage at 700° C. for one embodiment of the present invention versus a prior art electrode.

Although the present invention will be described as an oxygen sensor, it is understood that the sensor could be a nitrous oxide sensor, hydrogen sensor, hydrocarbon sensor, or the like. Furthermore, while oxygen is the reference gas used in the description disclosed herein, it should be understood that other gases could be employed as the reference gas.

The sensor of the present invention comprises a sensing electrode to sense an exhaust gas and a reference electrode to sense a reference gas with an electrolyte disposed there between. The sensor may further include other conventional elements such as leads, contact pads, heaters, support layers, and the like.

The solid electrolyte can comprise any material conventionally employed for sensor electrolytes, including, but not limited to, zirconia, such as yttria doped zirconia, ceria, strontium cerium oxide, barium cerium oxide, strontium cerium zirconates, barium cerium zirconates.

At least one, preferably both of the electrodes disposed on or adjacent to the electrolyte comprises a metal such as a noble metal(s) and metal oxides. Possible metals include: platinum, gold, palladium, rhodium, iridium, osmium, ruthenium and mixtures and alloys including at least one of these metals; and other metals. Combined with the noble metal are metal oxides of at least zirconia and alumina, and optionally other metal oxides such as ceria, calcia, yttria, magnesia, lanthana and mixtures and alloys thereof, and the like.

Typically, at least one preferably both electrodes comprise about 80 weight percent (wt %) to about 99.85 wt % noble metal; about 0.1 wt % to about 14 wt % metal oxide (excluding alumina), and about 0.05 wt % to about 6 wt % alumina, based upon the total weight of the electrode after sintering. Preferably, the electrode comprises about 84.5 wt % to about 96 wt % noble metal, about 0.5 wt % to about 11.5 wt % zirconia, and about 0.5 wt % to about 4 wt % alumina; with about 86.4 wt % to about 92 wt % noble metal, about 0.5 wt % to about 11.2 wt % zirconia and about 0.8 wt % to about 2.4 wt % alumina more preferred; with the zirconia preferably being yttria stabilized zirconia having up to about 15 wt % yttria, preferably up to about 5.5 wt % yttria based on the total weight of the zirconia and yttria.

Although the electrode(s) can be formed in a conventional fashion, it is preferable to prepare the electrode material in the form of ink, by forming a slurry, paste or the like, according to known techniques. For example, the noble metal, metal oxides and optionally binders, plasticizers, fugitive material, etc., can be mixed in a sufficient quantity of solvent to attain the desired viscosity level for the particular processing technique. Possible solvents include terpineol, ethanol, xylenes, toluene, methyl ethyl ketone (MEK), and the like Once prepared, the ink can be applied to the desired area of the oxygen sensor, typically the electrolyte or a layer adjacent to the electrolyte such as a dielectric layer, through conventional techniques such as screen printing, painting, spraying, or the like. Once the ink has been applied, screen printed tiles are typically air dried in a convection oven at about 80° C. to about 100° C. for up to about 10 minutes.

Prior to sintering, the dried electrode composition generally comprises about 75 wt % to about 90 wt % noble metal, about 0.8 wt % to about 11 wt % metal oxide, about 0.1 wt % to an amount above which the resistivity of the electrode is too high (e.g., typically a resistivity above about 500 milliohms/square at room temperature (about 25° C.)) of alumina, and up to about 15 wt % of fugitive material (including any dried organic constituents, binders, etc.); with about 75 wt % to about 85 wt % of noble metal, about 5.2 wt % to about 10.5 wt % metal oxide, about 0.5 wt % to about 2.5 wt % alumina, and about 11 wt % to about 13.5 wt % fugitive material preferred; and about 75 wt % to about 80 wt % noble metal about 6.5 wt % to about 8.0 wt % zirconia, about 0.1 wt % to about 0.5 wt % yttria, about 1.5 wt % to about 2.1 wt % alumina, and about 13.0 wt % to about 13.5 wt % fugitive material more preferred. Preferably, the metal oxide comprises about 5 wt % to about 10 wt % zirconia and up to about 1.5 wt % yttria, with about 6.5 wt % to about 8.0 wt % zirconia and about 0.1 wt % to about 0.5 wt % yttria preferred, and about 0.2 wt % to about 0.4 wt % yttria especially preferred, based on the total weight of the dried electrode.

Referring to FIG. 1, the sensor comprises a pumping cell and a reference cell. The pumping cell comprises an electrolyte (1) disposed between an outer electrode (5) and an inner electrode (6). Disposed on the side of said sensing electrode (4), opposite said electrolyte (1), is a protective layer (3). Meanwhile, on the side of the said inner electrode (6), opposite the electrolyte (1) is a porous diffusion restriction (8), adjacent the reference cell. The reference cell comprises the sensing electrode (4) and reference electrode (7), with electrolyte (1') disposed therebetween. On the side of the reference electrode (7) opposite the electrolyte (1') are support layers (2), ground plane (11), heater (12), and protective layer (13). The electrodes (4,5,6,7) are connected to contacts (9,10), via leads (14,15,16). It should be noted that the support layers (2), ground plane (11), heater(s) (12), contacts (9,10) and leads (14,15,16) can be composed of materials conventionally used in automotive sensors.

For example, the support layers can comprise a metal oxide, such as alumina, while the heaters, leads and contacts comprise a thermally and electrically conductive metal such as precious metals, e.g. platinum, palladium, and the like.

In one embodiment, during use, the sensor is typically disposed in the stream to be sensed, e.g., the exhaust stream. Based upon the condition of the stream, i.e. rich or lean, oxygen is pumped in or out of the sensor by the pumping cell. The increase/decrease, accordingly, of creates an oxygen partial pressure difference between the oxygen at the sensing electrode and that at the reference electrode, thereby developing an electromotive force.

The following example is provided to further illustrate the present invention and not to limit the generally broad scope hereof.

EXAMPLE

The following example was employed to form reference and sensing electrodes comprising 47.20 wt % platinum, 4.90 wt % zirconia; 0.2.5 wt % yttria; 1.29 wt % alumina, 6.36 wt % carbon black, 2.00 wt % ethocellulose (binder), 38.00 wt % terpineol (solvent).

For example, the ink, was prepared by mixing 4.720 grams(g) platinum, 0.644 g 3 mole % yttria doped zirconia containing 20 wt % alumina, and 0.636 g submicron sized carbon black powder with 4.000 g terpineol/ethocellulose based solvent to form a paste. The paste was spatula mixed and then further dispersed using a 3-roll mill.

Electrode test sheets were then formed by screen printing the electrode tapes onto an unfired, "green" zirconia substrate using a, 325 mesh screen and a 1-mil emulsion. An additional sheet of 5 mole % yttria doped zirconia solid electrolyte tape was then placed between two electrode test sheets such that the printed electrodes were on the outer faces of the 3 stacked sheets. The sheets were vacuum bagged and laminated in an isostatic lamination unit for 10 minutes at 85° C. at 4,000 pounds per square inch (psi). Once cooled to room temperature, disks were cut from the laminate by end mill singulation. The disks were then sintered in a kiln in atmospheric air at about 1,300° C. to 1,550° C. The firing cycle was a 10 hour ramp to 500° C., a 5 hour ramp from 500° C. to 1500° C., and a 2 hour hold at 1500° C. The disks were cooled to room temperature and tested for electrical performance.

Figure 4:
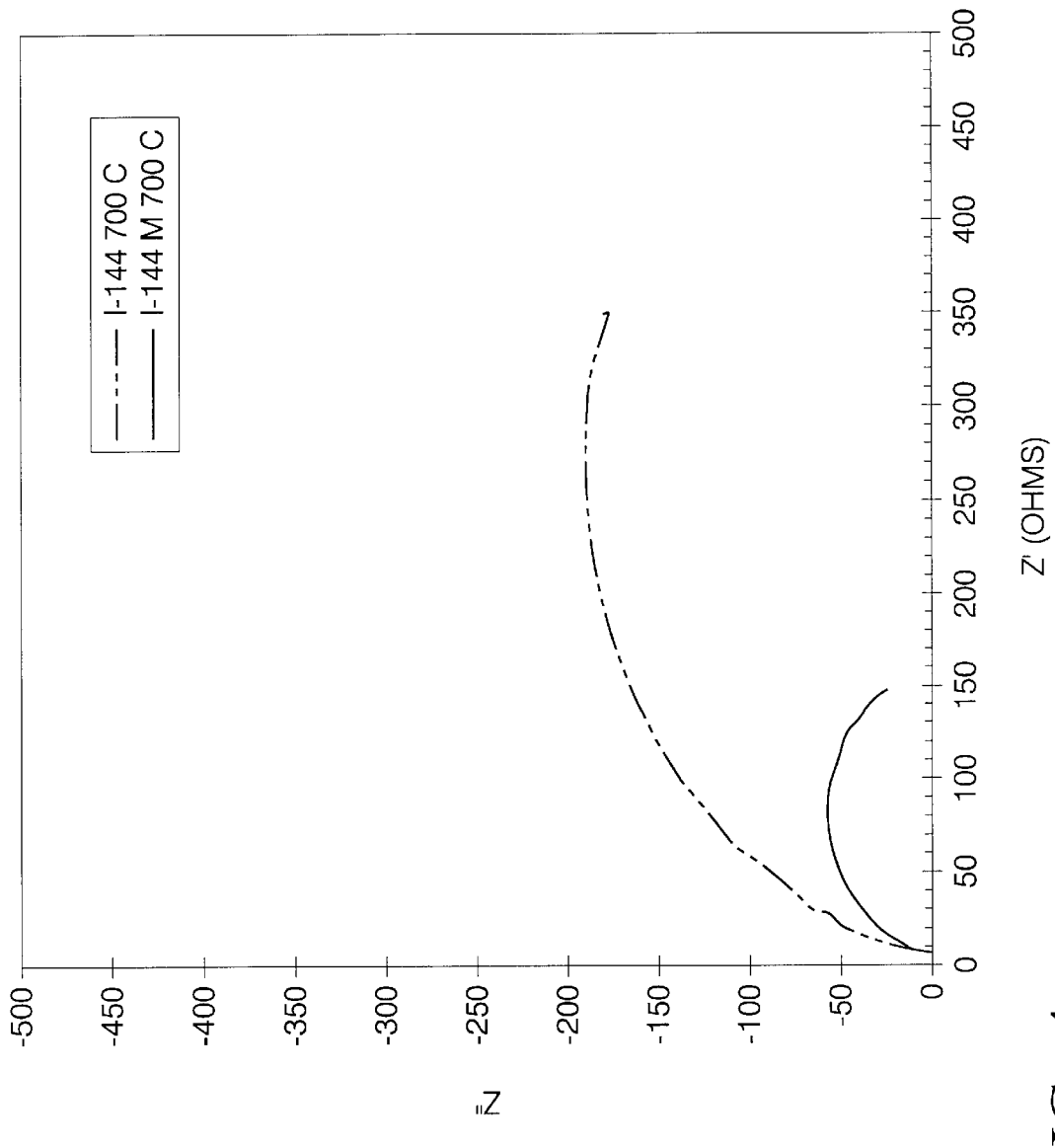
FIG. 4 a graphical representation of electrode ink impedance for one embodiment of the present invention versus a prior art electrode.

Electrical performance testing comprised loading the disks into a kiln and heating to 800° C. in air with the electrodes connected to the outside of the kiln via platinum leadwires. A complex impedance measurement, as shown in FIG. 4, was then made using an impedance analyzer. The wire leads were nulled and a frequency sweep from 2 mega hertz ("MHz") to 0.1 hertz ("Hz"), at 50 millivolt ("mV") amplitude, 0 volt ("V") bias, was made on the disk. Temperatures at about 700° C. to about 800° C. were preferred to see the characteristic electrode arc that is plotted on a real ($Z^1$) vs. imaginary axis ($Z^{11}$) (see FIG. 4). The point at which the arc intercepts the X (real) axis reveal; the sum of the grain plus grain boundary impedance and the total cell impedance (grain+grain boundary+electrode). The difference between the two intercepts represents the electrode impedance. As can be seen, a low total impedance of 163 ohms was achieved which results in a better performance and current density of the cell, compared with 526 ohms achieved with the prior art electrode; a nearly 70% impedance reduction. Consequently, the sensor of the present invention reduces the impedance by over 60%, from above about 500 ohms for conventional sensors to below about 200 ohms for the present invention, with below about 175 ohms preferred, and below about 165 ohms especially preferred.

Figure 3:
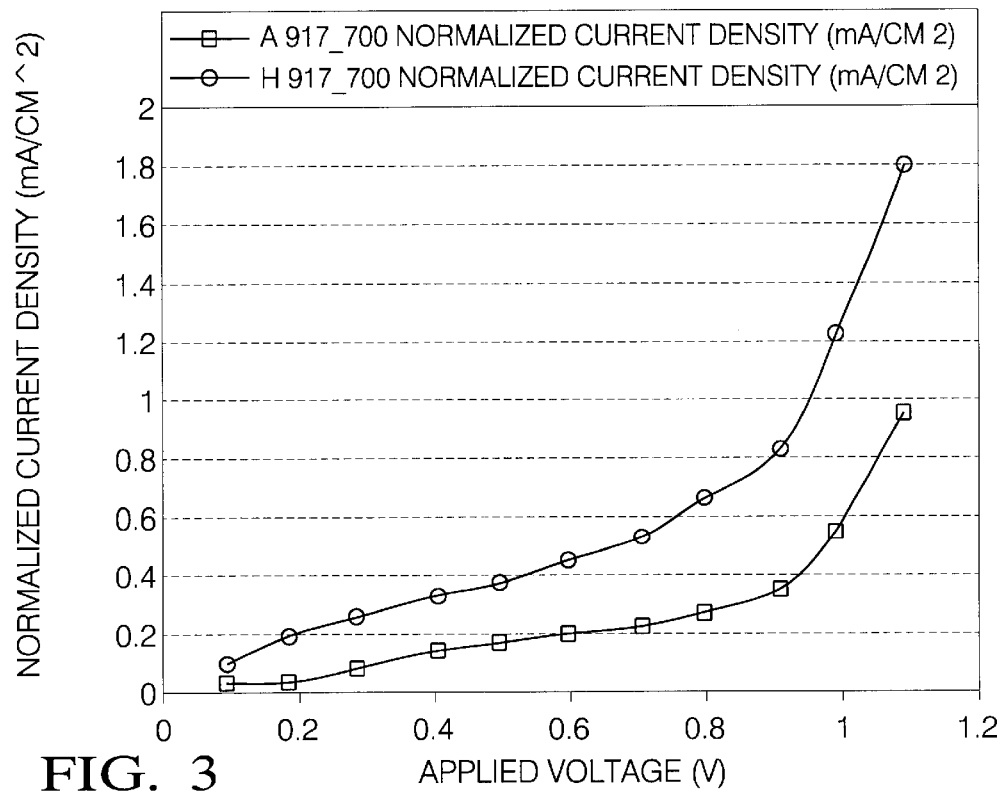
FIG. 3 a graphical representation of current density versus applied voltage at 700° C. for one embodiment of the present invention versus a prior art electrode.

A voltage vs. current measurement, as illustrated in FIG. 3, was also performed. This measurement was made by applying the voltage across the cell and measuring the resultant cell's pumping current by stepping the voltage between 0 and 1 volts (V) in 0.1 V increments. Each step was held for about 30 seconds, and the average current generated by the cell was calculated by measuring the voltage across a precision resistor, which is typically about 10 to about 100 ohms, in series, in the test circuit. As is illustrated in FIG. 3, the example electrode, line 10, possess a higher current as a function of the voltage than the conventional electrode, line 12.

The bulk resistivity was calculated by measuring the electrode diameter and the sample thickness. The disk geometries of the different specimens were matched to enable a direct comparison of the cell complex impedance and the voltage vs. current resistance.

The electrode ink formulation and the resultant electrode are but one feature that will determine the behavior of the cell. The electrolyte also plays a large role. Aside from the compositional effects, it may provide a source of impurities that can strongly influence the cell performance. Alumina additions to yttria stabilized zirconia bodies provide a gettering effect, tying up silicon based impurities and promoting better electrolyte conductivity. This alumina gettering effect is apparent in the electrode of the present invention, showing improved electrical performance over like electrodes without alumina; i.e. gettering of impurities, particularly those associated with silicate-based glassy phases present in the electrode or electrolyte body is achieved by adding alumina to the metal oxide, e.g. yttria stabilized zirconia.

This invention overcomes some of the shortcomings that exist in the prior art. impurities can result in a high electrode/electrolyte interfacial impedance. This high impedance (e.g. greater than about 500 ohms) effect from impurities that migrate to the electrode/electrolyte interface associated with the silica based glassy phases is overcome by the present electrode. Furthermore, the gettering effect of alumina in the ink formulation results in a higher conductivity of the cell as a whole.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A sensor, comprising:
   a sensing electrode having a first electrical lead and positioned to sense a sensing gas;
   a reference electrode having a second electrical lead; and
   an electrolyte disposed between and in intimate contact with said sensing electrode and said reference electrode;

wherein at least one of said sensing electrode and said reference electrode comprises about 86.4 wt % to about 92 wt % noble metal, about 0.5 wt % to about 11.2 wt % zirconia, and about 0.8 wt % to about 2.4 wt % alumina, based upon the total weight of the electrode.

2. The sensor of claim 1, wherein said zirconia is yttria doped zirconia comprising up to 15 wt % yttria based upon the total weight of the zirconia and yttria.

3. The sensor of claim 1, wherein said electrode has an impedance below about 200 ohms.

4. A method of sensing exhaust gas, comprising:

using a sensor comprising a sensing electrode having a first electrical lead, a reference electrode having a second electrical lead, and an electrolyte disposed between and in intimate contact with said sensing electrode and said reference electrode; wherein at least one of said sensing electrode and said reference electrode comprises about 86.4 wt % to about 92 wt % noble metal, about 0.5 wt % to about 11.2 wt % zirconia, and about 0.8 wt % to about 2.4 wt % alumina, based upon the total weight of the electrode;

disposing said sensor in an exhaust stream; and contacting said sensing electrode with exhaust gas.

* * * * *